United States Patent [19]

Payne et al.

[11] Patent Number: 5,296,368

[45] Date of Patent: Mar. 22, 1994

[54] *BACILLUS THURINGIENSIS* ISOLATE DENOTED *B.T.* PS81F, ACTIVE AGAINST LEPIDOPTERAN PESTS, AND A GENE ENCODING A LEPIDOPTERAN-ACTIVE TOXIN

[75] Inventors: Jewel Payne; August J. Sick, both of San Diego, Calif.

[73] Assignee: Mycogen Corporation, San Diego, Calif.

[21] Appl. No.: 978,839

[22] Filed: Nov. 19, 1992

Related U.S. Application Data

[62] Division of Ser. No. 629,504, Dec. 18, 1990.

[51] Int. Cl.$^5$ ............... C12N 5/00; C12N 15/00; C12P 21/00; C12P 21/04
[52] U.S. Cl. ................ 435/240.4; 435/69.1; 435/70.1; 435/172.3
[58] Field of Search ........... 424/93; 435/172.3, 252.3, 435/69.1, 70.1, 240.4; 800/205; 536/27

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |

FOREIGN PATENT DOCUMENTS 9010076 9/1990 PCT Int'l Appl. .

OTHER PUBLICATIONS

Ohtani et al. Plant Mol. Biol., vol. 16 (1991) pp. 117–128.
Barton et al. Plant Physiol., vol. 85 (1987) pp. 1103–1109.
Vaeck et al. Nature, vol. 328 (1987) pp. 33–37.
Andrews et al. CRC. Crit. Rev. in Biotech., vol. 6 (1987) pp. 163–232.
Hoffman et al. Plant Mol. Biol., vol. 11 (1988) pp. 717–729.
Schnepf, H. Ernest, and H. R. Whiteley (1981) "Cloning and expression of the *Bacillus thuringiensis* crystal protein gene in *Escherichia coli*" Proc. Natl. Acad. Sci. USA 78(5);2893–2897.

*Primary Examiner*—David T. Fox
*Assistant Examiner*—Charles Rories
*Attorney, Agent, or Firm*—Saliwanchik & Saliwanchik

[57] ABSTRACT

A novel *B.t.* toxin gene toxic to lepidopteran insects has been cloned from a novel lepidopteran-active *B. thuringiensis* microbe. The DNA encoding the *B.t.* toxin can be used to transform various prokaryotic and eukaryotic microbes to express the *B.t.* toxin. These recombinant microbes can be used to control lepidopteran insects in various environments.

1 Claim, 1 Drawing Sheet

A. *B.t.* PS81F uncut
B. *B.t.* PS81F cut with HindIII
C. *B.t.* HD-1 uncut
D. *B.t.* HD-1 cut with HindIII

BACILLUS THURINGIENSIS ISOLATE DENOTED B.T. PS81F, ACTIVE AGAINST LEPIDOPTERAN PESTS, AND A GENE ENCODING A LEPIDOPTERAN-ACTIVE TOXIN This is a continuation, division, of application Ser. No. 07/629,504 filed Dec. 18, 1990.

BACKGROUND OF THE INVENTION

The most widely used microbial pesticides are derived from the bacterium *Bacillus thuringiensis*. This bacterial agent is used to control a wide range of leaf-eating caterpillars, and mosquito *Bacillus thuringiensis* produces a proteinaceous paraspore or crystal which is toxic upon ingestion by a susceptible insect host. For example, *B. thuringiensis* var. *kurstaki* HD-1 produces a crystal called a delta toxin which is toxic to the larvae of a number of lepidopteran insects. The cloning and expression of this *B.t.* crystal protein gene in *Escherichia coli* has been described in the published literature (Schnepf, H.E. and Whitely, H.R. [1981]Proc. Natl. Acad. Sci. USA 78:2893-2897). U.S. Pat. No. 4,448,885 and U.S. Pat. No. 4,467,036 both disclose the expression of *B.t.* crystal protein in *E. coli*.

BRIEF SUMMARY OF THE INVENTION

The subject invention concerns a novel *Bacillus thuringiensis* isolate designated *B.t.* PS81F which has activity against all lepidopteran pests tested.

Also disclosed and claimed is a novel toxin gene toxic to lepidopteran insects. This toxin gene can be transferred to suitable hosts via a plasmid vector.

Specifically, the invention comprises a novel *B.t.* isolate denoted *B.t.* PS81F, mutants thereof, and a novel delta endotoxin gene which encodes a 133,266 dalton protein which is active against lepidopteran pests.

Table 1 discloses the DNA encoding the novel toxin. Table 2 discloses the amino acid sequence of the novel toxin. Table 3 is a composite of Tables 1 and 2. Table 4 shows a comparison of the deduced amino acid sequence of 81F with five other known *B.t.* endotoxins.

DETAILED DISCLOSURE OF THE INVENTION

Figure 1:
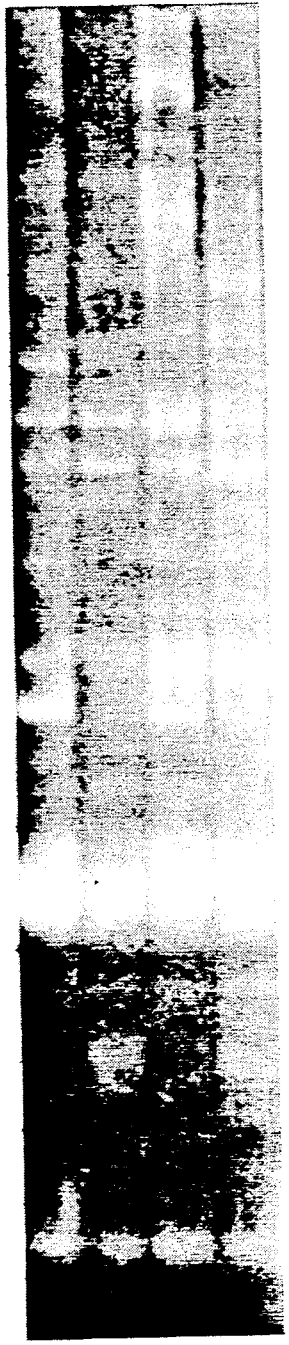
FIG. 1 shows a photograph of a stained gel produced by agarose gel electrophoresis of plasmid preparations from B.t. PS81F and *B.t.* HD-1.

The novel toxin gene of the subject invention was obtained from a novel lepidopteran-active *B. thuringiensis* (*B.t.*) isolate designated PS81F.

Characteristics of *B.t.* PS81F

Colony morphology——Large colony, dull surface, typical *B.t.*
Vegetative cell morphology——typical *B.t.*
Flagellar serotype——4a4c, kenya
Intracellular inclusions——sporulating cells produce a bipyramidal crystal.
Plasmid preparations——agarose gel electrophoresis of plasmid preparations distinguishes *B.t.* PS81F from *B.t.* HD-1 and other *B.t.* isolates.
Alkali-soluble proteins——*B.t.* PS81F has a 130,000 dalton protein and a 60,000 dalton protein.
Activity——*B.t.* PS81F kills all Lepidoptera tested.

| Bioassay results: | |
|---|---|
| | LC50 |
| Beet armyworm, *Spodoptera exigua* | 10.4 ug/ml |
| Western spruce budworm, *Choristoneura occidentalis* | 1.4 ug/ml |

Bioassay procedures:
*Spodoptera exigua*——dilutions are prepared of a spore and crystal pellet, mixed with USDA Insect Diet (Technical Bulletin 1528, U.S. Department of Agriculture) and poured into small plastic trays. Neonate *Spodoptera exigua* larvae are placed on the diet mixture and held at 25° C. Mortality is recorded after six days.
*Choristoneura occidentalis*——dilutions and diet are prepared in the same manner as for the *Spodoptera exigua* bioassay. Fourth instar larvae are used, and mortality is recorded after eight days.

*B. thuringiensis* PS81F, NRRL B-18424, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against *Lepidoptera*, e.g., caterpillars. *B.t.* PS81F, and mutants thereof, can be used to control lepidopteran pests.

A subculture of *B.t.* PS81F and the *E. coli* host harboring the toxin gene of the invention, *E. coli* DH5($\alpha$), containing the plasmid pMYC386, was deposited in the permanent collection of the Northern Research Laboratory, U.S. Department of Agriculture, Peoria, Ill., USA on Oct. 7, 1988. The accession numbers are as follows:

*B.t.* PS81F NRRL B—18424
*E. coli* (DH5$\alpha$) (pMYC386) NRRL B—18423

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a w±de variety of microbial hosts. Expression of the toxin gene results, directly or indirectly, in the intracellular production and maintenance of the pesticide. With suitable hosts, e.g., *Pseudomonas*, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonhs, Erwinia, Serratia, Klebsiella, Xanthomonas, Streptomyces, Rhizobium, Rhodopseudomonas, Methylophilius, Agrobacterium, Acetobacter, Lactabacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and Aureobasidium. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W.H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81F can be made by procedures well known in the art. For example, an asporogenous mutant can be obtained through ethylmethane sulfonate (EMS) mutagenesis of PS81F. The mutants can be made using ultraviolet light and nitrosoguanidine by procedures well known in the art.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS81F, NRRL B-18424

A subculture of B.t. PS81F, NRRL B-18424, or mutants thereof, can be used to inoculate the following medium, a peptone, glucose, salts medium.

| | |
|---|---|
| Bacto Peptone | 7.5 g/l |
| Glucose | 1.0 g/l |

| -continued | |
|---|---|
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Gene and into *Escherichia coli*

Total cellular DNA was prepared by growing the cells of B. thuringiensis HD-1 and the novel B.t. PS81F to a low optical density (OD$_{600}$=1.0) and recovering the cells by centrifugation. The cells were protoplasted in TES buffer (30 mM Tris-Cl, 10 mM EDTA, 50 mM NaCl, pH=8.0) containing 20 % sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was extracted twice with phenol/chloroform (1:1). The DNA was precipitated in ethanol and purified by isopycnic banding on a cesium chloride gradient.

Total cellular DNA from each (PS81F and HD-1) was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986]Gene USA 43:29–40). These two fragments were combined and used as the probe. Results show that hybridizing fragments of PS81F are distinct from those of HD-1. Specifically, a 3.5 Kb hybridizing band in PS81F was detected instead of the 300 bp larger 3.8 Kb hybridizing band seen in HD-1.

Two hundred micrograms of PS81F total cellular DNA was digested with EcoRI and separated by electrophoresis on a preparative 0.8% Agarose-TAE gel. The 3.0 Kb to 4.0 Kb region of the gel was cut out and the DNA from it was electroeluted and concentrated using an ELUTIP TM-d (Schleicher and Schuell, Keene, NH) ion exchange column. The isolated EcoRI fragments were ligated to LAMBDA ZAP TM EcoRI arms (Stratagene Cloning Systems, La Jolla, CA) and packaged using GIGAPACK GOLD TM extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BLUESCRIPT TM (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, designated pM5,31-1, contained an approximate 3.5 Kb EcoRI insert and was sequenced using Stratagene's T7 and T3 primers plus a set of existing *B.t.* endotoxin oligonucleotide primers. About 1.7 Kb of the toxin gene was sequenced and data analysis comparing PS81F to other cloned *B.t.* endotoxin genes showed that the PS81F sequence was unique. A synthetic oligonucleotide (GCTGAAGAACTTC-CTATTCGTGGTGGTGAGC) was constructed to one of the regions in the PS81F sequence that was least homologous relative to other existing *B.t.* endotoxin genes.

Total cellular DNA partially digested with Sau3A and fractionated by electrophoresis into a mixture of 9-23 Kb fragments on a 0.6% agarose TAE gel was ligated into LAMBDA DASH TM (Stratagene). The packaged phage were plated out with P2392 *E. coli* cells (Stratagene) at a high titer and screened using the radiolabeled synthetic oligonucleotide supra as a nucleic acid hybridization probe. Hybridizing plaques were rescreened at a lower plaque density. A purified hybridizing plaque was used to infect P2392 *E. coli* cells in liquid culture for preparation of phage for DNA isolation. DNA was isolated by standard procedures. Preparative amounts of recombinant phage DNA were digested with SalI (to release the inserted DNA from lambda arms) and separated by electrophoresis on a 0.6% Agarose-TAE gel. The large fragments (electroeluted and concentrated as described above) were ligated to an XhoI digested and phosphatased BLUESCRIPT TM plasmid. The ligation was transformed into *E. coli* DH5($\alpha$) competent cells (BRL) and plated on LB agar containing ampicillin, isopropyl-($\beta$)-D-thiogalactoside (IPTG) and 5-bromo-4-chloro-3-indolyl-($\beta$)-D-galactoside (XGAL). White colonies (with insertions in the ($\beta$)-galactosidase gene of pBluescript) were subjected to standard miniprep procedures to isolate the plasmid, designated pMI,43-24. The full length toxin gene was sequenced by using oligonucleotide primers made to the "4.3 Kb class" toxin gene and by "walking" with primers made to the sequence of PS81F. Data analysis comparing the deduced PS81F amino acid sequence to the sequences of five other endotoxins shows PS81F to be unique (Table 4).

The plasmid pM1,43-24 contains about 18 Kb of PS81F DNA including the 3.518 Kb which codes for the 133,266 dalton endotoxin. The plasmid was reduced in size by cutting out approximately 13 Kb of non-coding DNA, ligating the ends, transforming DH5($\alpha$) and plating on LB agar containing ampicillin. The resulting colonies were analyzed by standard miniprep procedures to isolate plasmids that were reduced in size. The desired plasmid, pMYC386, contains the coding sequence of the PS81F toxin gene, which could be excised as an SaeI to ApaI 4.5 Kb fragment.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E.F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, MD, or New England Biolabs, Beverly, MA. The enzymes are used according to the instructions provided by the supplier.

Plasmid pMYC386 containing the *B.t.* toxin gene, can be removed from the transformed host microbe by use of standard well-known procedures. For example, *E. coli* NRRL B-18423 can be subjected to cleared lysate isopycnic density gradient procedures, and the like, to recover pMYC386.

Data from standard insect tests show that novel *B.t.* PS81F is active against diamondback moth, *Spodoptera exigua*, Western spruce budworm, and *T. ni.*

EXAMPLE 3

Insertion of Toxin Gene Into Plants

The novel gene coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983]Cell 32:1033-1043). A particularly useful vector in this regard is pEND4K (Klee, H.J., Yanofsky, M.F. and Nester, E.W. [1985]Bio/Technology 3:637—642) This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4

Cloning of Novel *B. thuringiensis* Gene Into Baculoviruses

The novel gene of the invention can be cloned into baculoviruses such as *Autographa californica* nuclear polyhedrosis virus (AcNPV) Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G.D., Shoemaker, C. and Miller, L.K. [1984]Mol. Cell. Biol. 4:399–406), and pAC380, described by Smith et al. (Smith, G.E., Summers, M.D. and Fraser, M.J. [1983]Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel *B.t.* toxin gene is shown in Table 1. The deduced amino acid sequence is shown in Table 2.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATM | Asparagine (Asn) | AAK |
| Methonine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W- C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequence of the *B.t.* toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E.T. and Kezdy, F.J. [1984]Science 223:249–255). Thus, the subject invention includes mutants of the amino acid sequence depicted herein which do not alter the protein secondary structure, or if the structure is altered, the biological activity is retained to some degree.

TABLE 1

Nucleotide sequence of novel toxin encoding gene.

|  | 10 | 20 | 30 | 40 | 50 | 60 |
|---|---|---|---|---|---|---|
| 1 | ATGGAGATAG | TGAATAATCA | GAATCAATGC | GTGCCTTATA | ATTGTTTAAA | TAATCCTGAA |
| 61 | AATGAGATAT | TAGATATTGA | AAGGTCAAAT | AGTACTGTAG | CAACAAACAT | CGCCTTGGAG |
| 121 | ATTAGTCGTC | TGCTCGCTTC | CGCAACTCCA | ATAGGGGGGA | TTTTATTAGG | ATTGTTTGAT |
| 181 | GCAATATGGG | GGTCTATAGG | CCCTTCACAA | TGGGATTTAT | TTTTAGAGCA | AATTGAGCTA |
| 241 | TTGATTGACC | AAAAAATAGA | GGAATTCGCT | AGAAACCAGG | CAATTTCTAG | ATTAGAAGGG |
|  | 310 | 320 | 330 | 340 | 350 | 360 |
| 301 | ATAAGCAGTC | TGTACGGAAT | TTATACAGAA | GCTTTTAGAG | AGTGGGAAGC | AGATCCTACT |
| 361 | AATCCAGCAT | TAAAAGAAGA | GATGCGTACT | CAATTTAATG | ACATGAACAG | TATTCTTGTA |
| 421 | ACAGCTATTC | CTCTTTTTTC | AGTTCAAAAT | TATCAAGTCC | CATTTTTATC | AGTATATGTT |
| 481 | CAAGCTGCAA | ATTTACATTT | ATCGGTTTTG | AGAGATGTTT | CAGTGTTTGG | GCAGGCTTGG |
| 541 | GGATTTGATA | TAGCAACAAT | AAATAGTCGT | TATAATGATC | TGACTAGACT | TATTCCTATA |
|  | 610 | 620 | 630 | 640 | 650 | 660 |
| 601 | TATACAGATT | ATGCTGTACG | CTGGTACAAT | ACGGGATTAG | ATCGCTTACC | ACGAACTGGT |
| 661 | GGGCTGCGAA | ACTGGGCAAG | ATTTAATCAG | TTTAGAAGAG | AGTTAACAAT | ATCAGTATTA |
| 721 | GATATTATTT | CTTTTTTCAG | AAATTACGAT | TCTAGATTAT | ATCCAATTCC | AACAAGCTCC |
| 781 | CAATTAACGC | GGGAAGTATA | TACAGATCCG | GTAATTAATA | TAACTGACTA | TAGAGTTGGC |
| 841 | CCCAGCTTCG | AGAATATTGA | GAACTCAGCC | ATTAGAAGCC | CCCACCTTAT | GGACTTCTTA |
|  | 910 | 920 | 930 | 940 | 950 | 960 |
| 901 | AATAATTTGA | CCATTGATAC | GGATTTGATT | AGAGGTGTTC | ACTATTGGGC | AGGGCATCGT |
| 961 | GTAACTTCTC | ATTTTACAGG | TAGTTCTCAA | GTGATAACAA | CCCCTCAATA | TGGGATAACC |
| 1021 | GCAAATGCGG | AACCAAGACG | AACTATTGCT | CCTAGTACTT | TTCCAGGTCT | TAACCTATTT |
| 1081 | TATAGAACAT | TATCAAATCC | TTTCTTCCGA | AGATCAGAAA | ATATTACTCC | TACCTTAGGG |
| 1141 | ATAAATGTAG | TACAGGGAGT | AGGGTTCATT | CAACCAAATA | ATGCTGAAGT | TCTATATAGA |
|  | 1210 | 1220 | 1230 | 1240 | 1250 | 1260 |
| 1201 | AGTAGGGGGA | CAGTAGATTC | TCTTAATGAG | TTACCAATTG | ATGGTGAGAA | TTCATTAGTT |
| 1261 | GGATATAGTC | ATCGATTAAG | TCATGTTACA | CTAACCAGGT | CGTTATATAA | TACTAATATA |
| 1321 | ACTAGCCTGC | CAACATTTGT | TTGGACACAT | CACAGTGCTA | CTAATACAAA | TACAATTAAT |
| 1381 | CCAGATATTA | TTACACAAAT | ACCTTTAGTG | AAAGGATTTA | GACTTGGTGG | TGGCACCTCT |
| 1441 | GTCATTAAAG | GACCAGGATT | TACAGGAGGG | CATATCCTTC | GAAGAAATAC | CATTGGTGAG |
|  | 1510 | 1520 | 1530 | 1540 | 1550 | 1560 |
| 1501 | TTTGTGTCTT | TACAAGTCAA | TATTAACTCA | CCAATTACCC | AAAGATACCG | TTTAAGATTT |
| 1561 | CGTTATGCTT | CCAGTAGGGA | TGCACGAATT | ACTGTAGCGA | TAGGAGGACA | AATTAGAGTA |
| 1621 | GATATGACCC | TTGAAAAAAC | CATGGAAATT | GGGGAGAGCT | TAACATCTAG | AACATTTAGC |
| 1681 | TATACCAATT | TTAGTAATCC | TTTTTCATTT | AGGGCTAATC | CAGATATAAT | TAGAATAGCT |
| 1741 | GAAGAACTTC | CTATTCGTGG | TGGTGAGCTT | TATATAGATA | AAATTGAACT | TATTCTAGCA |
|  | 1810 | 1820 | 1830 | 1840 | 1850 | 1860 |
| 1801 | GATGCAACAT | TTGAAGAAGA | ATATGATTTG | GAAAGAGCAC | AGAAGGCGGT | GAATGCCCTG |
| 1861 | TTTACTTCTA | CAAATCAACT | AGGGCTAAAA | ACAGATGTGA | CGGATTATCA | TATTGATCAA |
| 1921 | GTTTCCAATT | TAGTTGAGTG | TTTATCGGAT | GAATTTTGTC | TGGATGAAAA | GAGAGAATTA |

TABLE 1-continued

Nucleotide sequence of novel toxin encoding gene.

| | | | | | | |
|---|---|---|---|---|---|---|
| 1981 | TCCGAGAAAG | TCAAACATGC | GAAGCGACTC | AGTGATGAAC | GGAATTTACT | TCAAGATCCA |
| 2041 | AACTTCAGAG | GGATCAATAG | GCAACCAGAC | CGTGGCTGGA | GAGGAAGCAC | GGATATTACT |
| | 2110 | 2120 | 2130 | 2140 | 2150 | 2160 |
| 2101 | ATCCAAGGTG | GAGATGACGT | ATTCAAAGAG | AATTACGTCA | CATTACCGGG | TACCTTTGAT |
| 2161 | GAGTGCTATC | CAACGTATTT | ATATCAAAAA | ATAGATGAGT | CGAAGTTAAA | AGCTTATACC |
| 2221 | CGCTATGAAT | TAAGAGGGTA | TATCGAGGAT | AGTCAAGACT | TAGAAATCTA | TTTAATTCGC |
| 2281 | TACAATGCAA | AACACGAGAC | AGTAAACGTG | CCAGGTACGG | GTTCCTTATG | GCCGCTTTCA |
| 2341 | GCCCAAAGTC | CAATCGGAAA | GTGTGGAGAA | CCGAATCGAT | GCGCGCCACA | CCTTGAATGG |
| | 2410 | 2420 | 2430 | 2440 | 2450 | 2460 |
| 2401 | AATCCTAATC | TAGATTGCTC | CTGCAGAGAC | GGGGAAAAAT | GTGCCCATCA | TTCCCATCAT |
| 2461 | TTCTCCTTGG | ACATTGATGT | TGGATGTACA | GACTTAAATG | AGGACTTAGG | TGTATGGGTG |
| 2521 | ATATTCAAGA | TTAAGACACA | AGATGGCTAT | GCAAGACTAG | GAAATCTAGA | GTTTCTCGAA |
| 2581 | GAGAAACCAC | TATTAGGGGA | AGCACTAGCT | CGTGTGAAAA | GAGCGGAGAA | AAAATGGAGA |
| 2641 | GACAAATGCG | AAAAATTGGA | ATGGGAAACA | AATATTGTTT | ATAAAGAGGC | AAAAGAATCT |
| | 2710 | 2720 | 2730 | 2740 | 2750 | 2760 |
| 2701 | GTAGATGCTT | TATTTGTAAA | CTCTCAATAT | GATAGATTAC | AAGCGGATAC | GAATATCGCG |
| 2761 | ATGATTCATG | CGGCAGATAA | ACGCGTTCAT | AGCATTCGAG | AAGCGTATCT | GCCAGAGCTG |
| 2821 | TCTGTGATTC | CGGGTGTCAA | TGCGGCTATT | TTTGAAGAAT | TAGAAGGGCG | TATTTTCACT |
| 2881 | GCATTCTCCC | TATATGATGC | GAGAAATGTC | ATTAAAAATG | GCGATTTCAA | TAATGGCTTA |
| 2941 | TCATGCTGGA | ACGTGAAAGG | GCATGTAGAT | GTAGAAGAAC | AGAACAACCA | TCGTTCGGTC |
| | 3010 | 3020 | 3030 | 3040 | 3050 | 3060 |
| 3001 | CTTGTTGTTC | CAGAATGGGA | AGCAGAAGTG | TCACAAGAAG | TTCGTGTTTG | TCCGGGTCGT |
| 3061 | GGCTATATCC | TTCGTGTTAC | AGCGTACAAA | GAGGGATATG | GAGAGGGCTG | TGTAACGATT |
| 3121 | CATGAGATCG | AAGACAATAC | AGACGAACTG | AAATTCAGCA | ACTGTGTAGA | AGAGGAAGTA |
| 3181 | TATCCAAACA | ACACGGTACA | GTGTAATAAT | TATACTGCGA | CTCAAGAAGA | ACATGAGGGT |
| 3241 | ACGTACACTT | CCCGTAATCG | AGGATATGAC | GAAGCCTATG | AAAGCAATTC | TTCTGTACAT |
| | 3310 | 3320 | 3330 | 3340 | 3350 | 3360 |
| 3301 | GCGTCAGTCT | ATGAAGAAAA | ATCGTATACA | GATAGACGAA | GAGAGAATCC | TTGTGAATCT |
| 3361 | AACAGAGGAT | ATGGGGATTA | CACACCACTA | CCAGCTGGCT | ATGTGACAAA | AGAATTAGAG |
| 3421 | TACTTCCCAG | AAACCGATAA | GGTATGGATT | GAGATCGGAG | AAACGGAAGG | AACATTCATC |
| 3481 | GTGGACAGCG | TGGAATTACT | TCTTATGGAG | GAATAATA | | |

TABLE 2

Deduced amino acid sequence of novel toxin.

|   |   |   |   |   | 5 |   |   |   |   | 10 |   |   |   |   | 15 |
|---|---|---|---|---|---|---|---|---|---|---|---|---|---|---|---|
| 1 | Met | Glu | Ile | Val | Asn | Asn | Gln | Asn | Gln | Cys | Val | Pro | Tyr | Asn | Cys |
| 16 | Leu | Asn | Asn | Pro | Glu | Asn | Glu | Ile | Leu | Asp | Ile | Glu | Arg | Ser | Asn |
| 31 | Ser | Thr | Val | Ala | Thr | Asn | Ile | Ala | Leu | Glu | Ile | Ser | Arg | Leu | Leu |
| 46 | Ala | Ser | Ala | Thr | Pro | Ile | Gly | Gly | Ile | Leu | Leu | Gly | Leu | Phe | Asp |
| 61 | Ala | Ile | Trp | Gly | Ser | Ile | Gly | Pro | Ser | Gln | Trp | Asp | Leu | Phe | Leu |
| 76 | Glu | Gln | Ile | Glu | Leu | Leu | Ile | Asp | Gln | Lys | Ile | Glu | Glu | Phe | Ala |
| 91 | Arg | Asn | Gln | Ala | Ile | Ser | Arg | Leu | Glu | Gly | Ile | Ser | Ser | Leu | Tyr |
| 106 | Gly | Ile | Tyr | Thr | Glu | Ala | Phe | Arg | Glu | Trp | Glu | Ala | Asp | Pro | Thr |
| 121 | Asn | Pro | Ala | Leu | Lys | Glu | Glu | Met | Arg | Thr | Gln | Phe | Asn | Asp | Met |
| 136 | Asn | Ser | Ile | Leu | Val | Thr | Ala | Ile | Pro | Leu | Phe | Ser | Val | Gln | Asn |
| 151 | Tyr | Gln | Val | Pro | Phe | Leu | Ser | Val | Tyr | Val | Gln | Ala | Ala | Asn | Leu |
| 166 | His | Leu | Ser | Val | Leu | Arg | Asp | Val | Ser | Val | Phe | Gly | Gln | Ala | Trp |
| 181 | Gly | Phe | Asp | Ile | Ala | Thr | Ile | Asn | Ser | Arg | Tyr | Asn | Asp | Leu | Thr |
| 196 | Arg | Leu | Ile | Pro | Ile | Tyr | Thr | Asp | Tyr | Ala | Val | Arg | Trp | Tyr | Asn |
| 211 | Thr | Gly | Leu | Asp | Arg | Leu | Pro | Arg | Thr | Gly | Gly | Leu | Arg | Asn | Trp |
| 226 | Ala | Arg | Phe | Asn | Gln | Phe | Arg | Arg | Glu | Leu | Thr | Ile | Ser | Val | Leu |
| 241 | Asp | Ile | Ile | Ser | Phe | Phe | Arg | Asn | Tyr | Asp | Ser | Arg | Leu | Tyr | Pro |
| 256 | Ile | Pro | Thr | Ser | Ser | Gln | Leu | Thr | Arg | Glu | Val | Tyr | Thr | Asp | Pro |
| 271 | Val | Ile | Asn | Ile | Thr | Asp | Tyr | Arg | Val | Gly | Pro | Ser | Phe | Glu | Asn |
| 286 | Ile | Glu | Asn | Ser | Ala | Ile | Arg | Ser | Pro | His | Leu | Met | Asp | Phe | Leu |
| 301 | Asn | Asn | Leu | Thr | Ile | Asp | Thr | Asp | Leu | Ile | Arg | Gly | Val | His | Tyr |
| 316 | Trp | Ala | Gly | His | Arg | Val | Thr | Ser | His | Phe | Thr | Gly | Ser | Ser | Gln |
| 331 | Val | Ile | Thr | Thr | Pro | Gln | Tyr | Gly | Ile | Thr | Ala | Asn | Ala | Glu | Pro |
| 346 | Arg | Arg | Thr | Ile | Ala | Pro | Ser | Thr | Phe | Pro | Gly | Leu | Asn | Leu | Phe |
| 361 | Tyr | Arg | Thr | Leu | Ser | Asn | Pro | Phe | Phe | Arg | Arg | Ser | Glu | Asn | Ile |
| 376 | Thr | Pro | Thr | Leu | Gly | Ile | Asn | Val | Val | Gln | Gly | Val | Gly | Phe | Ile |
| 391 | Gln | Pro | Asn | Asn | Ala | Glu | Val | Leu | Tyr | Arg | Ser | Arg | Gly | Thr | Val |
| 406 | Asp | Ser | Leu | Asn | Glu | Leu | Pro | Ile | Asp | Gly | Glu | Asn | Ser | Leu | Val |
| 421 | Gly | Tyr | Ser | His | Arg | Leu | Ser | His | Val | Thr | Leu | Thr | Arg | Ser | Leu |
| 436 | Tyr | Asn | Thr | Asn | Ile | Thr | Ser | Leu | Pro | Thr | Phe | Val | Trp | Thr | His |
| 451 | His | Ser | Ala | Thr | Asn | Thr | Asn | Thr | Ile | Asn | Pro | Asp | Ile | Ile | Thr |
| 466 | Gln | Ile | Pro | Leu | Val | Lys | Gly | Phe | Arg | Leu | Gly | Gly | Gly | Thr | Ser |
| 481 | Val | Ile | Lys | Gly | Pro | Gly | Phe | Thr | Gly | Gly | Asp | Ile | Leu | Arg | Arg |
| 496 | Asn | Thr | Ile | Gly | Glu | Phe | Val | Ser | Leu | Gln | Val | Asn | Ile | Asn | Ser |
| 511 | Pro | Ile | Thr | Gln | Arg | Tyr | Arg | Leu | Arg | Phe | Arg | Tyr | Ala | Ser | Ser |
| 526 | Arg | Asp | Ala | Arg | Ile | Thr | Val | Ala | Ile | Gly | Gln | Ile | Ile | Arg | Val |
| 541 | Asp | Met | Thr | Leu | Glu | Lys | Thr | Met | Glu | Ile | Gly | Glu | Ser | Leu | Thr |
| 556 | Ser | Arg | Thr | Phe | Ser | Tyr | Thr | Asn | Phe | Ser | Asn | Pro | Phe | Ser | Phe |
| 571 | Arg | Ala | Asn | Pro | Asp | Ile | Ile | Arg | Ile | Ala | Glu | Glu | Leu | Pro | Ile |
| 586 | Arg | Gly | Gly | Glu | Leu | Tyr | Ile | Asp | Lys | Ile | Glu | Leu | Ile | Leu | Ala |
| 601 | Asp | Ala | Thr | Phe | Glu | Glu | Glu | Tyr | Asp | Leu | Glu | Arg | Ala | Gln | Lys |
| 616 | Ala | Val | Asn | Ala | Leu | Phe | Thr | Ser | Thr | Asn | Gln | Leu | Gly | Leu | Lys |
| 631 | Thr | Asp | Val | Thr | Asp | Tyr | His | Ile | Asp | Gln | Val | Ser | Asn | Leu | Val |

TABLE 2-continued

Deduced amino acid sequence of novel toxin.

| | | | | | | | | | | | | | | |
|---|---|---|---|---|---|---|---|---|---|---|---|---|---|---|
| 646 | Glu | Cys | Leu | Ser | Asp | Glu | Phe | Cys | Leu | Asp | Glu | Lys | Arg | Glu | Leu |
| 661 | Ser | Glu | Lys | Val | Lys | His | Ala | Lys | Arg | Leu | Ser | Asp | Glu | Arg | Asn |
| 676 | Leu | Leu | Gln | Asp | Pro | Asn | Phe | Arg | Gly | Ile | Asn | Arg | Gln | Pro | Asp |
| 691 | Arg | Gly | Trp | Arg | Gly | Ser | Thr | Asp | Ile | Thr | Ile | Gln | Gly | Gly | Asp |
| 706 | Asp | Val | Phe | Lys | Glu | Asn | Tyr | Val | Thr | Leu | Pro | Gly | Thr | Phe | Asp |
| 721 | Glu | Cys | Tyr | Pro | Thr | Tyr | Leu | Tyr | Gln | Lys | Ile | Asp | Glu | Ser | Lys |
| 736 | Leu | Lys | Ala | Tyr | Thr | Arg | Tyr | Glu | Leu | Arg | Gly | Tyr | Ile | Glu | Asp |
| 751 | Ser | Gln | Asp | Leu | Glu | Ile | Tyr | Leu | Ile | Arg | Tyr | Asn | Ala | Lys | His |
| 766 | Glu | Thr | Val | Asn | Val | Pro | Gly | Thr | Gly | Ser | Leu | Trp | Pro | Leu | Ser |
| 781 | Ala | Gln | Ser | Pro | Ile | Gly | Lys | Cys | Gly | Glu | Pro | Asn | Arg | Cys | Ala |
| 796 | Pro | His | Leu | Glu | Trp | Asn | Pro | Asn | Leu | Asp | Cys | Ser | Cys | Arg | Asp |
| 811 | Gly | Glu | Lys | Cys | Ala | His | His | Ser | His | His | Phe | Ser | Leu | Asp | Ile |
| 826 | Asp | Val | Gly | Cys | Thr | Asp | Leu | Asn | Glu | Asp | Leu | Gly | Val | Trp | Val |
| 841 | Ile | Phe | Lys | Ile | Lys | Thr | Gln | Asp | Gly | Tyr | Ala | Arg | Leu | Gly | Asn |
| 856 | Leu | Glu | Phe | Leu | Glu | Glu | Lys | Pro | Leu | Leu | Gly | Glu | Ala | Leu | Ala |
| 871 | Arg | Val | Lys | Arg | Ala | Glu | Lys | Lys | Trp | Arg | Asp | Lys | Cys | Glu | Lys |
| 886 | Leu | Glu | Trp | Glu | Thr | Asn | Ile | Val | Tyr | Lys | Glu | Ala | Lys | Glu | Ser |
| 901 | Val | Asp | Ala | Leu | Phe | Val | Asn | Ser | Gln | Tyr | Asp | Arg | Leu | Gln | Ala |
| 916 | Asp | Thr | Asn | Ile | Ala | Met | Ile | His | Ala | Ala | Asp | Lys | Arg | Val | His |
| 931 | Ser | Ile | Arg | Glu | Ala | Tyr | Leu | Pro | Glu | Leu | Ser | Val | Ile | Pro | Gly |
| 946 | Val | Asn | Ala | Ala | Ile | Phe | Glu | Glu | Leu | Glu | Gly | Arg | Ile | Phe | Thr |
| 961 | Ala | Phe | Ser | Leu | Tyr | Asp | Ala | Arg | Asn | Val | Ile | Lys | Asn | Gly | Asp |
| 976 | Phe | Asn | Asn | Gly | Leu | Ser | Cys | Trp | Asn | Val | Lys | Gly | His | Val | Asp |
| 991 | Val | Glu | Glu | Gln | Asn | Asn | His | Arg | Ser | Val | Leu | Val | Val | Pro | Glu |
| 1006 | Trp | Glu | Ala | Glu | Val | Ser | Gln | Glu | Val | Arg | Val | Cys | Pro | Gly | Arg |
| 1021 | Gly | Tyr | Ile | Leu | Arg | Val | Thr | Ala | Tyr | Lys | Glu | Gly | Tyr | Gly | Glu |
| 1036 | Gly | Cys | Val | Thr | Ile | His | Glu | Ile | Glu | Asp | Asn | Thr | Asp | Glu | Leu |
| 1051 | Lys | Phe | Ser | Asn | Cys | Val | Glu | Glu | Glu | Val | Tyr | Pro | Asn | Asn | Thr |
| 1066 | Val | Thr | Cys | Asn | Asn | Tyr | Thr | Ala | Thr | Gln | Glu | Glu | His | Glu | Gly |
| 1081 | Thr | Tyr | Thr | Ser | Arg | Asn | Arg | Gly | Tyr | Asp | Glu | Ala | Tyr | Glu | Ser |
| 1096 | Asn | Ser | Ser | Val | His | Ala | Ser | Val | Tyr | Glu | Glu | Lys | Ser | Tyr | Thr |
| 1111 | Asp | Arg | Arg | Arg | Glu | Asn | Pro | Cys | Glu | Ser | Asn | Arg | Gly | Tyr | Gly |
| 1126 | Asp | Tyr | Thr | Pro | Leu | Pro | Ala | Gly | Tyr | Val | Thr | Lys | Glu | Leu | Glu |
| 1141 | Tyr | Phe | Pro | Glu | Thr | Asp | Lys | Val | Trp | Ile | Glu | Ile | Gly | Glu | Thr |
| 1156 | Glu | Gly | Thr | Phe | Ile | Val | Asp | Ser | Val | Glu | Leu | Leu | Leu | Met | Glu |
| 1171 | Glu | | | | | | | | | | | | | | |

TABLE 3

| | | | | 5 | | | | 10 | | | | | 15 | | | | 20 |
|---|---|---|---|---|---|---|---|---|---|---|---|---|---|---|---|---|---|
| Met ATG | Glu GAG | Ile ATA | Val GTG | Asn AAT | Asn AAT | Gln CAA | Asn AAT | Val GTG | Cys TGC | Tyr TAT | Pro CCT | Asn AAT | Leu TTA | Cys TGT | Asn AAT | Pro CCT | Glu GAA |
| | | | | | | | | | 30 | | | | 35 | | | | 40 |
| Asn AAT | Glu GAG | Ile ATA | Leu TTA | Asn AAT | Ile ATT | Gln CAG | Ser TCA | Asn AAT | Asp GAT | Ile ATT | Thr ACT | Val GTA | Thr ACA | Ala GCA | Ile ATC | Leu TTG | Glu GAG |
| | | | | 45 | | | | 50 | | | | | 55 | | | | 60 |
| Ile ATT | Ser AGT | Ile ATA | Leu CTG | Asp GAT | Ala GCT | Glu GAA | Ser TCC | Asn AAT | Pro CCA | Gly GGG | Val GTA | Ile ATT | Thr ACA | Leu TTA | Gly GGA | Phe TTT | Asp GAT |
| | | | | 65 | | | | 70 | | | | | 75 | | | | 80 |
| Ala GCA | Ile ATA | Arg CGT | Gly GGG | Leu CTC | Ala GCT | Ile ATA | Ser TCC | Ile ATA | Trp TGG | Gly GGA | Ile ATA | Leu TTA | Leu TTA | Phe TTT | Leu TTG | Phe TTT | Leu CTA |
| | | | | 85 | | | | 90 | | | | | 95 | | | | 100 |
| Leu TTG | Trp TGG | Asp GAC | Gln CAA | Ser TCT | Ile ATA | Ala GCT | Gly GGC | Gln CAA | Gln CAA | Phe TTC | Arg CGT | Glu GAG | Leu TTA | Ala GCA | Gln CAA | Glu GAA | Gly GGG |
| | | | | 105 | | | | 110 | | | | | 115 | | | | 120 |
| Ile ATA | Ser AGT | Ser AGT | Ala GCA | Lys AAA | Ile ATA | Ala GCT | Gly GGC | Ala GCT | Ala GCT | Thr ACT | Arg AGA | Ala GCA | Glu GAG | Ile ATT | Leu TTG | Glu GAA | Gly GGG |
| | | | | 125 | | | | 130 | | | | | 135 | | | | 140 |
| Asn AAT | Pro CCA | Ala GCA | Ile ATT | Tyr TAC | Gly GGA | Glu GAA | Gly GGG | Leu TTA | Glu GAG | Phe TTT | Asn AAT | Asp GAC | Ala GCA | Trp TGG | Arg AGA | Asp GAT | Thr ACT |
| | | | | 145 | | | | 150 | | | | | 155 | | | | 160 |
| Thr ACA | Ala GCT | Ala GCA | Ala GCA | Lys AAA | Leu CTT | Ser TCA | Ser TCA | Thr ACT | Leu CTG | Arg CGT | Gln CAA | Val GTT | Tyr TAT | Met ATG | Pro CCA | Ile ATT | Val GTA |
| | | | | 165 | | | | 170 | | | | | 175 | | | | 180 |
| Gln CAA | Gly GGA | Ile ATT | Ser AGT | Leu CTT | Ser TCA | Leu TTA | Ile ATT | Ser TCG | Leu TTA | Asn AAT | Arg AGA | Val GTC | Val GTC | Pro CCA | Ser TCA | Val GTA | Val GTT |
| | | | | 185 | | | | 190 | | | | | 195 | | | | 200 |
| Gly GGA | Phe TTT | Asp GAT | Ser TCA | Leu TTA | Leu TTA | Arg CGT | Arg AGA | Tyr TAT | Arg AGA | Tyr TAT | Val GTT | Ser TCA | Met ATG | Asp GAT | Phe TTT | Pro CCT | Trp TGG |
| | | | | 205 | | | | 210 | | | | | 215 | | | | 220 |
| Tyr TAT | Thr ACG | Arg CGA | Ala GCA | Ala GCA | Phe TTC | Arg AGA | Tyr TAT | Arg AGA | Tyr TAC | Thr ACG | Asp GAT | Leu CTG | Glu GAG | Thr ACT | Val GTA | Ile ATA | Ile ATA |
| | | | | 225 | | | | 230 | | | | | 235 | | | | 240 |
| Gly GGG | Leu CTG | Ile ATT | Arg AGA | Trp TGG | Ser TCT | Arg AGA | Phe TTT | Asn AAT | Gln CAG | Phe TTT | Thr ACA | Leu TTA | Arg CGC | Leu TTA | Ser TCA | Arg CGA | Gly GGT |
| | | | | 245 | | | | 250 | | | | | 255 | | | | 260 |
| Asp GAT | Leu TTA | Thr ACG | Ala GCA | Phe TTT | Val GTA | Ile ATT | Tyr TAC | Gln CAG | Asp GAT | Tyr TAT | Val GTA | Pro CCA | Leu TTA | Leu CTT | Thr ACA | Arg AGA | Leu TTA |
| | | | | 265 | | | | 270 | | | | | 275 | | | | 280 |
| Gln CAA | Leu TTA | Phe TTC | Arg AGA | Phe TTT | Ala GCT | Arg AGA | Tyr TAT | Asp GAT | Pro CCG | Thr ACA | Arg AGA | Pro CCA | Pro CCA | Thr ACT | Ile ATT | Thr ACA | Ser TCC |
| | | | | 285 | | | | 290 | | | | | 295 | | | | 300 |
| Pro CCC | Ser AGC | Phe TTC | Glu GAG | Glu GAA | Thr ACG | Gly GGT | Pro CCG | Ala GCC | Asn AAT | Ser AGC | Tyr TAT | Met ATG | Thr ACT | His CAC | Asp GAC | Thr ACA | Gly GGC |
| | | | | 305 | | | | 310 | | | | | 315 | | | | 320 |
| Asn AAT | Asn AAT | Leu TTG | His CAT | Asn AAT | Ser AGC | Val GTT | Ile ATT | Ala GCC | Gln CAG | Ile ATT | Val GTT | Ile ATA | His CAC | Leu CTT | Arg CGA | Gly GGG | Leu TTA |
| | | | | 325 | | | | 330 | | | | | 335 | | | | 340 |
| Thr ACT | Ser TCT | Arg CGG | His CAT | Phe TTT | Thr ACA | Thr ACA | Arg AGA | Ile ATT | Ile ATT | Pro CCC | Tyr TAT | Pro CCT | Tyr TAT | Trp TGG | Ser TCA | Arg AGA | Ser TCC |
| | | | | 345 | | | | 350 | | | | | 355 | | | | 360 |
| Val GTA | Thr ACT | His CAT | Glu GAG | Phe TTT | Pro CCT | Phe TTT | Ser TCT | Gln CAA | Ala GCA | Ile ATT | Tyr TAT | Pro CCT | Thr ACC | Gln CAA | Asp GAC | Gly GGG | Val GTT |
| Ala | Asn | Ala | Glu | Pro | Arg | Arg | Ile | Ala | Ser | Ile | Leu | Pro | Thr | Phe | Asn | Gly | Phe |

TABLE 3-continued

| | | | | | | | | | | | | | | | | | | | | Pos |
|---|---|---|---|---|---|---|---|---|---|---|---|---|---|---|---|---|---|---|---|---|
| GCA | Asn AAT | Ala GCG | Glu GAA | Pro CCA | Arg AGA | Pro CGA | Thr ACT | Ile ATT | Ala GCT | Pro CCT | Ser AGT | Thr ACT | Phe TTT | Pro CCA | Gly GGT | Leu CTT | Asn AAC | Leu CTA | Phe TTT | 380 |
| Tyr TAT | Arg AGA | Thr ACA | Leu TTA | Ser TCA | Gln CAG | Pro CCT | Phe TTC | Asn AAT | Arg CGA | Gln CAA | Asn AAT | Asn AAT | Asn AAT | Ile ATT | Thr ACT | Pro CCT | Thr ACC | Tyr TAT | Gly GGG | 400 |
| Ile ATA | Asn AAT | Val GTA | Val GTA | Gln CAG | Gly GGA | Val GTA | Gly GGG | Phe TTC | Ile ATT | Phe TTC | Asn AAT | Ala GCT | Asn AAT | Ala GCT | Glu GAA | Val GTT | Leu CTA | Tyr TAT | Arg AGA | 420 |
| Ser AGT | Arg AGG | Gly GGG | Thr ACA | Val GTA | Asp GAT | Ser TCT | Ile ATT | Asp GAT | Glu GAG | Ile ATT | Arg AGG | Ser TCG | Gly GGT | Gly GGT | Leu CTT | Val GTT | Ser TCA | Leu TTA | Val GTT | 440 |
| Gly GGA | Tyr TAT | Ser AGT | His CAT | Arg CGA | Thr ACA | Ser AGT | Arg AGG | Leu TTA | Thr ACA | His CAC | Leu CTA | Leu CTA | Leu CTA | Leu TTA | Tyr TAT | His CAT | Thr ACT | Asn AAT | Ile ATA | 460 |
| Thr ACT | Ser AGC | Leu CTG | Pro CCA | Thr ACA | Ile ATT | Leu CTG | His CAT | Trp TGG | Ser AGT | Ala GCT | Arg AGA | Thr ACT | Arg AGA | Asn AAT | Gly GGT | Ile ATT | Gly GGC | Thr ACC | Asn AAT | 480 |
| Pro CCA | Asp GAT | Ile ATT | Ile ATT | Thr ACA | Pro CCT | Gly GGA | Leu CTT | Gly GGA | Leu TTA | Val GTG | Ile ATT | Phe TTT | Arg AGA | Leu CTT | Thr ACC | Gly GGT | Gly GGC | Arg AGA | Ser TCT | 500 |
| Val GTC | Ile ATT | Gly GGA | Leu TTA | Pro CCA | Gln CAA | Phe TTT | Gly GGT | Gly GGG | Ser TCA | Ser AGC | Leu CTT | Arg AGA | Gln CAA | Arg AGA | Thr ACC | Ile ATT | Gly GGA | Arg AGA | Glu GAG | 520 |
| Phe TTT | Val GTG | Leu TTA | Leu TTA | Gln CAA | Asn AAC | Ala GCA | Met ATG | Phe TTT | Ile ATT | Thr ACC | Ala GCG | Ala GCG | Gln CAA | Gly GGG | Ser TCA | Arg AGA | Tyr TAC | Leu TTA | Phe TTT | 540 |
| Arg CGT | Tyr TAT | Ala GCT | Ser TCC | Ser AGT | Asp GAT | Met ATG | Ala GCA | Ile ATT | Val GTA | Ser AGC | Gly GGA | Ile ATA | Arg AGA | Val GTG | Ala GCG | Gly GGA | Arg AGA | Thr ACA | Val GTA | 560 |
| Asp GAT | Met ATG | Thr ACC | Leu CTT | Asn AAT | Thr ACC | Asp GAT | Phe TTT | Ala GCA | Arg AGA | Ser AGC | Thr ACA | Pro CCA | Lys AAG | Leu TTA | Ser TCT | Thr ACA | Phe TTT | Arg AGA | Ser AGC | 580 |
| Tyr TAT | Thr ACC | Ser TCC | Leu TTA | Ser AGT | Pro CCT | Thr ACC | Met ATG | Gly GGG | Arg AGG | Tyr TAT | Pro CCA | Lys AAG | Ile ATT | Glu GAA | Glu GAA | Val GTG | Phe TTT | Ile ATA | Ala GCT | 600 |
| Glu GAA | Glu GAA | Ala GCA | Leu TTA | Ile ATT | Glu GAA | Leu CTT | Phe TTT | Glu GAA | Tyr TAT | Gln CAA | Asn AAT | Gln CAG | Ala GCA | Ile ATT | Glu GAA | His CAT | Thr ACC | Leu CTA | Ala GCA | 620 |
| Asp GAT | Ala GCA | Thr ACA | Leu TTA | Ile ATT | Asp GAT | Leu CTA | Gly GGG | Glu GAA | Leu CTA | Thr ACA | Pro CCA | Lys AAG | Thr ACG | Leu CTG | Val GTG | Thr ACA | Arg AGA | Ala GCC | Leu CTG | 640 |
| Phe TTT | Ser TCC | Thr ACA | Phe TTT | Asn AAT | Cys TGT | Lys AAA | Leu TTA | Asp GAT | Lys AAA | Lys AAA | Asp GAT | Gln CAG | Asn AAT | Gln CAG | Thr ACG | His CAT | Lys AAG | Asp GAT | Gln CAA | 660 |
| Val GTT | Glu GAG | Asn AAT | Leu TTA | Val GTT | Ala GCG | Cys TGT | Leu CTA | Ala GCA | Asp GAT | Ser AGT | Ala GCA | Thr ACG | Leu CTG | Ser AGT | Leu CTG | Glu GAA | Leu TTA | Glu GAA | Leu TTA | 680 |
| Ser TCC | Lys AAA | Lys AAA | Val GTC | Lys AAA | Asn AAT | Ala GCG | Lys AAG | Ser AGT | Asp GAT | Leu CTC | Asp GAC | Asp GAT | Arg AGT | Asn AAT | Asp GAT | Arg CGG | Ala GCC | Asp GAT | Pro CCA | 700 |
| Asn AAC | Phe TTC | Arg AGA | Gly GGG | Ile ATC | Asn AAT | Arg AGG | Gln CAA | Gly GGC | Asp GAT | Pro CCA | Arg CGA | Trp TGG | Arg AGA | Gly GGA | Ser AGC | Gln CAA | Asp GAT | Ile ATT | Thr ACT | 720 |

TABLE 3-continued

| | | | | | | | | | | | | | |
|---|---|---|---|---|---|---|---|---|---|---|---|---|---|
| Ile ATC | Gln CAA | Gly GGT | Gly GGA | Asp GAC | Val GTA | Phe TTC | Lys AAA | Glu GAG | Tyr TAC | Val GTC | Thr ACA | Leu TTA | Asp GAT |
| | | | | | | | 730 | | | | | 735 | 740 |
| Glu GAG | Cys TGC | Tyr TAT | Pro CCA | Thr ACG | Leu TTA | Tyr TAT | Ile ATA | Asp GAT | Lys AAA | Ser TCG | Ala GCT | Lys AAG | Thr ACC |
| | | | | 745 | | | | 750 | | | | 755 | 760 |
| Arg CGC | Tyr TAT | Glu GAA | Leu TTA | Arg AGA | Tyr TAT | Ile ATC | Ser AGT | Glu GAG | Asp GAC | Leu TTA | Gly GGT | Pro CCG | Arg CGC |
| | | | | 765 | | | | 770 | | | | 775 | 780 |
| Tyr TAC | Asn AAT | Ala GCA | Lys AAA | His CAC | Thr ACA | Val GTA | Pro CCA | Val GTG | Asn AAC | Gly GGT | Cys TGC | Ser TCC | Ser TCA |
| | | | | 785 | | | | 790 | | | | 795 | 800 |
| Ala GCC | Gln CAA | Ser AGT | Pro CCA | Ile ATC | Gly GGA | Cys TGC | Lys AAG | Glu GAA | Arg CGA | Ala GCG | Leu CTT | Glu GAA | Trp TGG |
| | | | | 805 | | | | 810 | | | | 815 | 820 |
| Asn AAT | Pro CCT | Asn AAT | Leu CTA | Asp GAT | Cys TGT | Cys TGC | Asn AAT | Leu TTA | Arg AGA | Asp GAC | Ala GCC | His CAT | His CAT |
| | | | | 825 | | | | 830 | | | | 835 | 840 |
| Phe TTC | Ser TCC | Leu TTG | Asp GAC | Ile ATT | Lys AAG | Asp GAT | Thr ACA | Tyr TAT | Cys TGT | Gly GGA | Ala GCA | Asn AAT | Val GTG |
| | | | | 845 | | | | 850 | | | | 855 | 860 |
| Ile ATA | Phe TTC | Lys AAG | Ile ATT | Leu TTA | Gln CAA | Gly GGC | Asp GAT | Gly GGC | Leu CTA | Asn AAT | Glu GAG | Leu CTA | Glu GAA |
| | | | | 865 | | | | 870 | | | | 875 | 880 |
| Glu GAG | Lys AAA | Pro CCA | Leu CTA | Leu TTA | Gly GGG | Ala GCA | Tyr TAT | Ala GCT | Arg CGT | Lys AAA | Arg AGA | Ala GCA | Arg AGA |
| | | | | 885 | | | | 890 | | | | 895 | 900 |
| Asp GAC | Lys AAA | Cys TGC | Glu GAA | Leu TTG | Asn AAC | Trp TGG | Ser TCT | Arg AGA | Asn AAT | Val GTT | Tyr TAT | Lys AAA | Ser TCT |
| | | | | 905 | | | | 910 | | | | 915 | 920 |
| Val GTA | Asp GAT | Ala GCT | Asn AAC | Val GTA | Asp GAT | Ser AGC | Arg AGA | Tyr TAT | Gln CAA | Thr ACG | Ala GCG | Ile ATC | Ala GCG |
| | | | | 925 | | | | 930 | | | | 935 | 940 |
| Met ATG | Ile ATT | His CAT | Ala GCG | Gly GGG | Val GTA | Ala GCG | Lys AAA | His CAT | Val GTT | Glu GAA | Ala GCA | Leu CTG | Leu CTG |
| | | | | 945 | | | | 950 | | | | 955 | 960 |
| Ser TCT | Val GTG | Ile ATC | Pro CCG | Gly GGT | Asp GAT | Phe TTT | Ala GCT | Ile ATT | Ile ATT | Glu GAA | Arg CGT | Pro CCA | Thr ACT |
| | | | | 965 | | | | 970 | | | | 975 | 980 |
| Ala GCA | Phe TTC | Ser TCC | Leu CTA | Tyr TAT | Val GTC | Ala GCG | Asn AAT | Val GTA | Asp GAT | Ala GCG | Asn AAT | Ile ATC | Leu TTA |
| | | | | 985 | | | | 990 | | | | 995 | 1000 |
| Ser TCA | Cys TGC | Trp TGG | Asn AAC | Val GTG | Lys AAA | Asp GAT | Val GTA | Val GTA | Val GTC | Glu GAA | Ser TCA | Glu GAG | Val GTC |
| | | | | 1005 | | | | 1010 | | | | 1015 | 1020 |
| Leu CTT | Val GTT | Val GTT | Pro CCA | Leu CTA | Tyr TAT | Asp GAT | Val GTG | Asn AAT | Gln CAG | Leu TTA | His CAT | Pro CCG | Arg CGT |
| | | | | 1025 | | | | 1030 | | | | 1035 | 1040 |
| Gly GGC | Tyr TAT | Leu CTT | Leu CTA | Arg CGT | Leu CTT | Glu GAG | Lys AAA | Glu GAG | Gly GGA | Tyr TAT | Arg CGT | Val GTA | Ile ATT |
| | | | | 1045 | | | | 1050 | | | | 1055 | 1060 |
| His CAT | Glu GAG | Ile ATC | Glu GAA | Asp GAC | Asn AAT | Thr ACA | Asn AAT | Phe TTC | Ser AGC | Lys AAA | Cys TGT | Glu GAA | Val GTA |

TABLE 3-continued

| Tyr TAT | Pro CCA | Asn AAC | Asn AAC | 1065 Thr ACG | Val GTA | Thr ACG | Cys TGT | Asn AAT | 1070 Asn AAT | Tyr TAT | Thr ACT | Ala GCG | Thr ACT | 1075 Gln CAA | Glu GAA | Glu GAA | His CAT | Glu GAG | 1080 Gly GGT |
|---|---|---|---|---|---|---|---|---|---|---|---|---|---|---|---|---|---|---|---|
| Thr ACG | Tyr TAC | Thr ACT | Ser TCC | 1085 Arg CGT | Asn AAT | Arg CGA | Gly GGA | Tyr TAT | 1090 Asp GAC | Glu GAA | Ala GCC | Tyr TAT | Glu GAA | 1095 Ser AGC | Asn AAT | Ser TCT | Ser TCT | Val GTA | 1100 His CAT |
| Ala GCG | Ser TCA | Val GTC | Tyr TAT | 1105 Glu GAA | Glu GAA | Lys AAA | Ser TCG | Tyr TAT | 1110 Thr ACA | Asp GAT | Arg AGA | Arg GCA | Arg AGA | 1115 Glu GAG | Asn AAT | Pro CCT | Cys TGT | Glu GAA | 1120 Ser TCT |
| Asn AAC | Arg AGA | Gly GGA | Tyr TAT | 1125 Gly GGG | Asp GAT | Tyr TAC | Thr ACA | Pro CCA | 1130 Leu CTA | Pro CCA | Ala GCT | Gly GGC | Tyr TAT | 1135 Val GTG | Thr ACA | Lys AAA | Gly GGA | Leu TTA | 1140 Glu GAG |
| Tyr TAC | Phe TTC | Pro CCA | Glu GAA | 1145 Thr ACC | Asp GAT | Lys AAG | Val GTA | Trp TGG | 1150 Ile ATT | Glu GAG | Ile ATC | Gly GGC | Glu GAA | 1155 Thr ACG | Thr ACA | Gly GGA | Thr ACA | Phe TTC | 1160 Ile ATC |
| Val GTG | Asp GAC | Ser AGC | Val GTG | 1165 Glu GAA | Leu TTA | Leu CTT | Leu CTT | Met ATG | 1170 Glu GAG | Glu GAA | *** TAA | TA | | | | | | | |

TABLE 4

| | |
|---|---|
| HDE | -WHITELEY'S "4.5" GENE |
| HD73 | -ADANG'S "6.6" GENE |
| BTB | -BULLA'S "5.3" GENE |
| 81F | -MYCOGEN'S 81F TOX GENE |
| BTE | -HONEE'S ENTOMOCIDUS TOX GENE |
| HD2 | -BRIZZARD'S HD2 TOX GENE |

```
        1       5         10        15        20        25        30        35        40        45        50        55
HD1     M D N N P N I N E C I P Y N C L S N P E V E V L G G E R I E T G Y T P I D I S L S L T Q F L L S E F V P G A G
HD73    - - - - - - - - - - - - - - - - - - - - - - - - - - - - - - - - - - - - - - - - - - - - - - - - - - - - - - -
BTB     - - - - - - - - - - - - - - - - - - - - - - - - - - - - - - - - - - - - - - - - - - - - - - - - - - - - - - -
81F     - E I V N - Q - Q - V - - - - - N - - - N - I - D I - - S N S T = V A T N - A - E I S R = - - A S A T - T G -
BTE     - E E N N Q = - Q - - - - - - - - - - - E V L - D - - - - S - - N S S - - - - - - - V - - - V - N - - - - G -
HD2     - T S N R* - E - - I - N A V S N H S A Q M D L - P D A - - - D S* S T V Q T G I N I A G R I - G V L V - - F - -
                 * K                                                 * L C I S E G N N I D P F V S A 56      60        65        70        75        80        85        90        95        100       105       110
HD1     F V L G L V D I I W G I F G P S Q W D A F P V Q I E Q L I N Q R I E E F A R N Q A I S R L E G L S N L Y Q I Y
HD73    - - - - - - - - - - - - - - - - - - - - - L - - - - - - - - - - - - - - - - - - - - - - - - - - - - - - - - -
BTB     - - - - - - - - - - - - - - - - - - - - - L - - - - - - - - - - - - - - - - - - - - - - - - - - - - - - - - -
81F     I L - - - F - A - - - S I - - - - - - L - L E - - - L - - D - K - - - - - - - - - - - - - - - I - S - - G - -
BTE     - L V - - I - F V - - - V - - - - - - - - L - - - - - - - - - E - - G - - - - - A - - A N - - - - G - N F N - -
HD2     *Y S F = - - G E L - P R = - R D - - E I - L E H V - - - - - - Q - T - N - - - T - L A - - Q - - G D S F R A -
        * Q L A S F 111     115       120       125       130       135       140       145       150       155       160       165
HD1     A E S F R E W E A D P T N P A L R E E M R I Q F N D M N S A L T T A I P L L A V Q N Y Q V P L L S V Y V Q A A
HD73    - - - - - - - - - - - - - - - - - - - - - - - - - - - - - - - - - - - - - F - - - - - - - - - - - - - - - - -
BTB     - - - - - - - - - - - - - - - - - - - - - - - - - - - - - - - - - - - - - F - - - - - - - - - - - - - - - - -
81F     T - A - - - - - - - - - - - - - K - - - - T - - - - - - - I - V - - - - - F S - - - - - - - F - - - - - - - -
BTE     V - A - K - - - E - - N - - E T - T R V I D R - R I L D G L - E R D - - S F R I S G F E - - - - - - - A - - -
HD2     Q Q - L E D - L E N R D D A R T - S V L Y T - Y I A L E L D F L N - M - - F - I R - Q E - - - - M - - A - - -
```

```
                166                 170                 175                 180                 185                 190                 195                 200                 205                 210                 215                 220
HD1             G   P   D   S   R   D   W   V   R   Y   N   Q   F   R   R   E   L   T   L   T   V   L   D   I   V   A   L   F   S   N   Y   D   S   R   R   Y   P   I   R   T   V   S   Q   L   T   R   E   I   Y   T   N   P   V   L   E
HD73            -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -   -
BTB             T   -   -   -   -   -   -   -   L   -   -   -   -   -   -   -   -   -   -   -   -   -   -   -   -   -   -   -   S   -   -   -   -   -   -   -   -   -   -   -   -   -   P   -   S   -   -   -   -   -   -   -   -   -   N
81F             -   G   G   -   -   -   I   -   -   -   -   -   -   -   -   -   -   -   -   -   -   -   -   -   -   -   S   -   -   -   -   -   -   -   -   -   -   -   -   -   -   -   Q   P   -   -   -   -   -   -   D   -   I   -   -
BTE             K   -   T   Y   Q   -   -   -   A   -   -   -   -   -   -   -   -   -   -   -   -   -   -   -   -   A   -   F   -   -   -   -   -   -   -   -   -   -   -   -   T   -   -   -   -   -   -   -   -   -   -   D   -   L   -
HD2             -   T   N   A   A   A   -   -   -   -   -   -   -   -   -   -   -   -   -   -   -   -   -   -   -   L   -   -   -   -   -   -   -   -   -   -   -   -   -   -   -   -   N   -   S   A   -   -   -   -   -   D   A   Y   N
```

Sequence alignment (positions 331–495) for HD1, HD73, BTB, 81F, BTE, HD2.

Positions 331–385

|  | 331 | 335 | 340 | 345 | 350 | 355 | 360 | 365 | 370 | 375 | 380 | 385 |
|---|---|---|---|---|---|---|---|---|---|---|---|---|
| HD1  | GFSGPE | ==== FA | ==F FPPL | FGNA== PP | ==== ==== | ==== ==== | ==== ==SQ | ==== LTGL | ==IF ==== | RTLS SPLY | RRI= ==== | ==== |
| HD73 | ===== === | === === | === === | === === | === === | === === | === VS | === === | === === | === === | === === | === |
| BTB  | ==== T= | I== QS | === TY = | === === | === === | QQR = | =VA Q== | R=V = QQ | =V=Y ==Y | === == Y | === P= | === |
| 81F  | ==G === | SN= | ===  I= | =Y= | === ==A = | QR = | IV AQ T | I=P =Q N= | =V= L== | === N= | === PP | T== |
| BTE  | === T= | N== == | V= QV | IT= T= | === ==Q | Q=R = | =A PS | FFP = | =P =V | === === | =FF L= | === |
| HD2  | === G= | G== == | NT== L= | TSH = Y | T=AT N | T= SIN | T=R TF | AS FN | RD VY | E== == | =AG V= | N=T |

Positions 386–440

|  | 386 | 390 | 395 | 400 | 405 | 410 | 415 | 420 | 425 | 430 | 435 | 440 |
|---|---|---|---|---|---|---|---|---|---|---|---|---|
| HD1  | ==== IL GS | GP== QN | NQEL F | VLDGT EF | S=== FS | LTTS AY | GT NLP S | TI YRQ | R GT V | DSL DVI | EE LPP Q | DN SV P |
| HD73 | === F N= | === === | === === | === === | === === | === === | === === | === === | === === | === === | === === | === === |
| BTB  | === P | IQ | === | === | === | === | === | === | === | === | === | === |
| BTE  | L== W= | PW = | APR E | FNL RG | VQ GV | IST P | QP FT | VL = | AN* = | TTEL | DGE TT | == RK |
| HD2  | === L= | W = | LY EP | IHG VP | VR VE | NT SN | QNI = | SD = | *YS QP | YES PG | LQ LK | == D |

Positions 441–495

|  | 441 | 445 | 450 | 455 | 460 | 465 | 470 | 475 | 480 | 485 | 490 | 495 |
|---|---|---|---|---|---|---|---|---|---|---|---|---|
| HD1  | RAGFS HR | LSHV TML | SQA === | AGA VYT L | RAPT FS | WQHR S | AEF NNI | PSS QIT | QIPL T |
| HD73 | === === | === === | === === | === === | === === | === === | === === | === === | === === |
| BTB  | LVE == | VS == | F ==== | VS == | SI == | V == | H == | T === | AV = |
| 81F  | QQ L= | === == | SGFL YN | NN T=T | IM V== | T D= | TNT == | DP ER | IN V |
| BTE  | Y == | YG == | FRSS LY | SN TNT | V V= | T D= | LT T= | NPD ER | N = |
| HD2  | YES S | ===== | LIG I=A | RV R | V YY | G Y | L DR | T GP NR | D MV |

*Alignment is partial/approximate due to image density; "=" = identity to HD1 consensus; "—" = gap; "*" marks annotated residues.*

Sequence alignment (residues 661–825):

Block 1 (661–715):
```
          661                                                                                        715
HD1   S N Q I G L K T D V T D Y H I D Q V S N L V E C L S D E F C L D E K Q E L S E K V K H A K R L S D E R N L L Q
HD73  - - - - - - - - - - - - - - - - - - - - - - - - - - - - - - - - - - - - - - - - - - - - - - - - - - - - - -
BTB   - T - - - L - - - - - - - - - - - - - - - - - T - - - - - - - - - - - R - - - - - - - - - - - - - - - - - -
81F   - T - - - L - - - - - - - - - - - - - - - - - - D - - - - - - - - - - R - - - - - - - - - - - - - - - - - -
BTE   - T - - - - - - - - - - - - - - - - - - - - - Y A - - - - - - - - - - R - L - - - - - Y - - - - - - - - - -
HD2   - T - - - R R - - - - - - - - - - - - - - - - - - - - - - - - - - - - R - - - - - - - - - - - - - - - - - -
```

Block 2 (716–770):
```
          716                                                                                        770
HD1   D P N F R G I N R Q L D R G W R G S T D I T I Q G G D D V F K E N Y V T L L G T F D E C Y P T Y L Y Q K I D E
HD73  - S - - - - - - - - - - P E - - - - - - - - - - - - G - - - - - - - S - - - - - - - - - - - - - - - - - - -
BTB   - - - - - K D - - - - - P - - - - - - - - - - - - - - - - - - - - - - - - - - - - - - - - - - - - - - - - -
81F   - - - - - - - - - - - - P - - - - - - - - - - - - - - - - - - - - - - - - - - - P - V - - - - - - - - - - G
BTE   - - - - - - - T S - - - - R - - - - - - - - - - - - - - - - - - - - - - - - - P - N - - A - - - - - - - - -
HD2   - - - - - - - K - - P D*H - - - *F I S T N E Q S N F T S I H E Q S E - - W - - E N - - E - N - - - - - - - -
```

Block 3 (771–825):
```
          771                                                                                        825
HD1   S K L K A Y T R Y Q L R G Y I E D S Q D L E I Y L I R Y N A K H E T V N V P G T G S L W P L S A Q S P I G K C
HD73  - - - - - F - - - - - - - - - - - - - - - - - - - - - - - - - - - - - - - - - - - - - - - P - - - - - - - -
BTB   - - - - - - - - - - - - - - - E - - - - - - - - - - - - - - - - - - - - - I - - - - - - - - - - - - - - - -
81F   - E - - - - - - - - - - - - - E - - - - - - - - - - - - - - - - - - - - - - L D - - - - - - P - - - - - - -
BTE   - - - - - - - - - - - - - - - - - - - - - - - - - - - - - - - - - - - - - - - - - - - - - - V E - - - - - R
HD2   - - - - - - - - - - - - - - - - - - - - - - - - - - - - - - - - - - - - - - - - - - - - - - - - - - - - - -
```

Sequence alignment (positions 826–990):

```
                826       830       835       840       845       850       855       860       865       870       875       880
HD1             G E P N R C A P H L E W N P D L D C S C R D G E K C A H H S H H F S L D I D V G C T D L N E D L G V W V I F K
HD73            - - - - - - - - - - - - - - - - - - - - - - - - - - - - - - - - - - - - - - - - - - - - - - - - - - - - - - -
BTB             - - - - - - - - - - - - - - - - - - - - - - - - - - - - - - - - - - - - - - - - - - - - - - - - - - - - - - -
81F             - - - - - - - - - - - - - - N - - - - - - - - - - - - - - - - - - - - - - - - - - - - - H - - - - - - - - - -
BTE             - - - - - - - - - F - - - - - V - - - - - - - - - - - - - - - - - - - - - - - T - - - - - - N - - - - - - - -
HD2             - - - - - - - - - - - - - - - - - - - - - - - - - - - - - - - - - - - - - - - - - - - - - - - - - V - - - - -

881       885       890       895       900       905       910       915       920       925       930       935
HD1             I K T Q D G H A R L G N L E F L E E K P L V G E A L A R V K R A E K K W R D K R E K L E W E T N I V Y K E A K
HD73            - - - - - - - - - - - - - - - - - - - - - - - - - - - - - - - - - - - - - - - - - - - - - - - - - - - - - - -
BTB             - - - - - - - - - - - - - - - - - - - - - - - - - - - - - - - - - - - - - - - - - - - - - - - - - - - - - - -
81F             - - - - E - - - Y - - - - - - - - - - - - - - - - - - - - - - - - - - - - - - - - - - - - - - - - - - - - - - -
BTE             - - - - - - - - - - - - - - - - - - - - L L - - - - - - - - - - - - - - - - - - - - - - - - - - - - - - - - - -
HD2             - - - - - - - - - - - - - - - - - - - I - - - - - - - - - S - - - - - - - - - - - - C - - Q L Q L - - - K R - T 936       940       945       950       955       960       965       970       975       980       985       990
HD1             E S V D A L F V N S Q Y D Q L Q A D T N I A M I H A A D K R V H S I R E A Y L P E L S V I P G V N A A I F E E
HD73            - - - - - - - - - - - - - - - - - - - - - - - - - - - - - - - - - - - - - - - - - - - - - - - - - - - - - - -
BTB             - - - - - - - - - - - - - - R - - - - - - - - - - - - - - - - - - - - - - - - - - - - - - - - - - - - - - - - -
81F             - - - - - - - - - - - - - R - - - - - - - - - - - - - - - L - - - - - R - - - - - - - - - - - - - - - - - - - -
BTE             - - - - - - - V - - - - - R - - - - - - - - - - - - - - - - - - - - - - - - - - - - - - - - - - - - - - - - - -
HD2             - A - - - - - - - D - - - R - - - - - - - - - - - - - - - - - - - - R - - - - - - - - - P - - - - - - - - - E -
```

```
        991                                                                      1045
HD1     L E G R I F T A F S L Y D A R N V I K N G D F N N G L S C W N V K G H V D V E E Q N N Q R S V L V P E W E A
HD73    - - - - - - - - - - - - - - - - - - - - - - - - - - - - - - - - - - - - - - - - - - - - - - - V - - - -
BTB     - - - - H - - - - - - Y - - - - - - - - - - - - - - - - - - - - - - - H - - - - - - - H - - - V - - - -
81F     - - - - H - - - - - - I - - - - - - - - - - - - - - - L - - - - - - - H - - - - - - - H - - - I - - - -
BTE     - - - - - - - - - - - - - - - - - - - - - - - - - - - T - - - - - - - H - - - - = - - H - - - - - - - -
HD2     - - - - - - - - - - - - - - - - - V - - - - - - - - - - - - - - - - - - - - Q - - - - S - D - - - - - -

1046                                                                     1100
HD1     E V S Q E V R V C P G R G Y I L R V T A Y K E G Y G E G C V T I H E I E N N T D E L K F S N C V E E E I Y P N
HD73    - - - - - - - - - - - - - - - - - - - - - - - - - - - - - - - - - - - - - - - - - - - - - - - - - - - - -
BTB     - - - - - - - - - - - - - - - - - - - - - - - - - - - - - - - - - - - - - D - - - - - - - - - - - - - - -
81F     - - - - - - - - - - - - - - - - - - - - - - - - - - - - - - - - - - - - - D - - - - - - - - - - - - - - -
BTE     - - - - - - - - - - - - - - - - - - - - - - - - - - - - - - - - - - - - - - - - - - - - - - - V - - - - -
HD2     - - - - - - - - A - - - - - - - - - - - - - - - - - - - - - - - - - - - - - - - - - - - K - R E - V - - T 1101                                                                     1155
HD1     N T V T C N D Y T V N Q E E Y G G A Y T S R N R G Y N E A = = = P S V P A D Y A S V Y E E K S Y T D G R R
HD73    - - - - - - - - - - - - - - - - - - - - - - - - - - - = = = S N E - - - - - - - - - - - - - - - - - -
BTB     - - - N - - - - - A T - - - E - - E - - T - - - - D G - Y E S N E - - - N S S V H - - - A - - - - - R -
81F     - - - N - - - - - A T - - - H E - - E - - T - - - Q - D - - Y G N N R - - N S - - - - - - - A - - - - - -
BTE     - - - - - - - - - G T - - - E - - E - - T - - - - E D - Y E V D T T A S V N - K P T - - - E T - - - V -
HD2     D - G - - - - - - A H - G T A - * D - C N - A - * C A
```

|       | 1156 |   |   |   | 1160 |   |   |   |   | 1165 |   |   |   |   | 1170 |   |   |   |   | 1175 |   |   |   |   | 1180 |   |   |   |   | 1185 |   |   |   |   | 1190 |   |   |   |   | 1195 |   |   |   |   |   |   |   |   |   |   |
|-------|------|---|---|---|------|---|---|---|---|------|---|---|---|---|------|---|---|---|---|------|---|---|---|---|------|---|---|---|---|------|---|---|---|---|------|---|---|---|---|------|---|---|---|---|---|---|---|---|---|---|
| HD1   | N | P | C | E | F | N | R | G | Y | R | D | Y | T | P | L | P | V | G | Y | V | T | K | E | L | E | Y | F | P | P | E | T | D | K | V | W | I | E | I | G | E | T | E | G | T | F | I | V | D | S | V | E | L | L | M | E |
| HD73  | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — | — |
| BTB   | — | — | — | — | S | — | — | — | — | — | — | — | — | — | — | A | — | — | — | — | — | — | — | — | — | — | — | — | — | — | — | — | — | — | — | — | — | — | — | — | — | — | — | — | — | — | — | — | — | — | — | — | — | — | — |
| 81F   | — | — | — | — | S | — | — | — | — | — | G | — | — | — | — | A | — | — | — | — | — | — | — | — | — | — | — | — | — | — | — | — | — | — | — | — | — | — | — | — | — | — | — | — | — | — | — | — | — | — | — | — | — | — | — |
| BTE   | — | — | — | — | S | — | — | — | — | — | G | — | — | — | — | A | — | — | — | — | — | — | — | D | — | — | — | — | — | — | — | — | — | — | — | — | — | — | — | — | — | — | — | — | — | — | — | — | — | — | — | — | — | — | — |
| HD2   | — | H | — | — | Y | D | — | — | — | — | V | N | Y | P | — | A | — | — | — | V | — | — | — | — | — | — | — | — | — | — | — | — | T | — | — | — | — | — | — | — | — | — | — | — | — | — | K | — | — | — | — | — | — | — | — |

HD1 is the cryA1 toxin gene from Bacillus thuringiensis subsp. kurstaki HD1 (Brizzard and Whiteley, Nucleic acids Reseach 16(1988)2723.
HD73 is the cryA3 gene from HD73.
BTB is the cryA2 gene from BT strain Berliner.
81F is a delta endotoxin gene from Mycogen's BT strain PS81F.
BTE is a delta endotoxin gene from BT subspecies entomocidus (Honee, Salm and Visser, Nucleic Acids Research 16(1988)6240.
HD2 is a delta endotoxin gene from BT strain HD2 (Brizzard and Whiteley, Nucleic Acids Research 16(1988)2723.
— — — — denote identical amino acid homologies.
= = = = denote gaps required to align sequences with HD1.
*denote inserts required to align the sequences BTE and HD2 with HD1.

We claim:

1. A plant cell transformed to express a gene encoding a protein having the amino acid sequence shown in Table 2.

* * * * *

UNITED STATES PATENT AND TRADEMARK OFFICE
CERTIFICATE OF CORRECTION

PATENT NO. : 5,296,368  Page 1 of 2
DATED : March 22, 1994
INVENTOR(S) : Jewel Payner, et al It is certified that error appears in the above-indentified patent and that said Letters Patent is hereby corrected as shown below:

| | |
|---|---|
| Column 1: | line 14: "mosquitoes" should read --mosquitoes.--. |
| Column 3: | line 6: "w±de" should read --wide--; line 39: "Pseudomonhs" should read --*Pseudomonas*--. |
| Column 8: | line 28: "and into" should read --and transformation into--. |
| Column 10: | line 42: "3:637--642)" should read --3:637-642).--; line 55: "(AcNPV)" should read --(AcNPV).--. |
| Column 11: | line 27: "3letter" should read --3-letter--. |
| Table 1: | at nucleotide 1471: "CATATCCTTC" should read --GATATCCTTC--. |
| Table 3: | triplet #226: "CGA" should read --GCA--; |

UNITED STATES PATENT AND TRADEMARK OFFICE
CERTIFICATE OF CORRECTION

PATENT NO. : 5,296,368
DATED : March 22, 1994
INVENTOR(S) : Jewel Payner, et al

It is certified that error appears in the above-indentified patent and that said Letters Patent is hereby corrected as shown below:

Table 4:      line 1: "HDE" should read --HD1--; position 53 of 81F: "T" should read --I--; position "170" is denoted twice, the second one should read --175--; position 226 of HD2: "A" should read --S--; position 292 of BTB: "R" should read --G--; position 317 of BTB: "Y" should read --E--; position 393 of HD73: "=" should read -- -- --; position 393 of BTB: "=" should read -- -- --; beginning at position 716 of 81F: should be all one line; position 751 of HD73: "S" should read -- -- --; position 753 of HD73: " -- " should read --S--; position 823 of HD2: "R" should read -- -- --; position 824 of HD2: " -- " should read --R--; position 986 of HD2: " -- " should read --E--; position 987 of HD2: "E" should read -- -- --; between positions 1105 and 1115: "1100" should read --1110--.

Signed and Sealed this

Sixteenth Day of August, 1994

Attest:

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO. : 5,296,368
DATED : March 22, 1994
INVENTOR(S) : Jewel Payne, August J. Sick It is certified that error appears in the above-identified patent and that said Letters Patent is hereby corrected as shown below:

Col. 23

Table 3:   triplet # 1113:   "GCA" should read --CGA--.

Signed and Sealed this

First Day of November, 1994

Attest:

BRUCE LEHMAN

Attesting Officer

Commissioner of Patents and Trademarks